(12) United States Patent
Bizup et al.

(10) Patent No.: US 7,972,314 B2
(45) Date of Patent: Jul. 5, 2011

(54) VENOUS ACCESS PORT BASE

(75) Inventors: Raymond R. Bizup, Feasterville, PA (US); Kevin Sanford, Chalfont, PA (US)

(73) Assignee: Medical Components, Inc., Harleysville, PA (US)

( * ) Notice: Subject to any disclaimer, the term of this patent is extended or adjusted under 35 U.S.C. 154(b) by 336 days.

(21) Appl. No.: 11/725,750

(22) Filed: Mar. 20, 2007

(65) Prior Publication Data
US 2007/0233018 A1   Oct. 4, 2007

Related U.S. Application Data

(60) Provisional application No. 60/786,976, filed on Mar. 29, 2006.

(51) Int. Cl.
*A61M 37/00* (2006.01)
(52) U.S. Cl. .......... 604/288.01; 604/288.02; 604/288.04
(58) Field of Classification Search . 604/288.01–288.04
See application file for complete search history.

(56) References Cited

U.S. PATENT DOCUMENTS

| | | | |
|---|---|---|---|
| 3,211,431 A | 10/1965 | Meysembourg et al. | |
| 4,634,427 A * | 1/1987 | Hannula et al. | 604/288.02 |
| 4,710,167 A | 12/1987 | Lazorthes | |
| 4,904,241 A * | 2/1990 | Bark | 604/288.02 |
| 5,006,115 A | 4/1991 | McDonald | |
| 5,360,407 A | 11/1994 | Leonard | |
| 5,743,873 A | 4/1998 | Cai et al. | |
| 5,755,780 A | 5/1998 | Finch, Jr. et al. | |
| 5,906,592 A | 5/1999 | Kriesel et al. | |
| 5,951,512 A | 9/1999 | Dalton | |
| 6,113,572 A | 9/2000 | Gailey et al. | |
| 6,827,709 B2 | 12/2004 | Fujii | |
| 6,997,914 B2 | 2/2006 | Smith et al. | |

FOREIGN PATENT DOCUMENTS

| | | |
|---|---|---|
| DE | 42 25 524 A1 | 2/1994 |
| DE | 295 12 576 U1 | 10/1995 |
| WO | WO 97/01370 | 1/1997 |

OTHER PUBLICATIONS

International Search Report, dated Dec. 17, 2007; PCT/US07/06957 (3 pages).
Written opinion, dated Dec. 17, 2007; PCT/US07/06957 (3pages).
EP Application No. 07753574.8, Reply, filed Nov. 30, 2010, 12 pages.
EP Application No. 07753574.8, Communication, dated May 21, 2010, 1 page.
EP Application No. 07753574.8, Extended Search Report, dated Feb. 15, 2010, 6 pages.
PCT Application No. PCT/US07/06957, International Preliminary Report on Patentability, dated Jun. 5, 2008, 5 pages.

* cited by examiner

*Primary Examiner* — Nicholas D Lucchesi
*Assistant Examiner* — Rebecca E Eisenberg
(74) *Attorney, Agent, or Firm* — Blank Rome LLP

(57) ABSTRACT

A venous access port having a port body, a septum, a chamber and a discharge port with a passageway extending therethrough outwardly from the chamber. The central region of the chamber is elevated with respect to the periphery of the chamber floor adjacent the chamber side wall and may be convex or conical, with the chamber floor periphery defining a vortex flow path.

7 Claims, 1 Drawing Sheet

VENOUS ACCESS PORT BASE

CROSS-REFERENCE TO RELATED APPLICATIONS

This application claims priority from U.S. Provisional Patent Application Ser. No. 60/786,976 filed Mar. 29, 2006.

FIELD OF THE INVENTION

This relates to the field of medical devices and more particularly to venous access ports.

BACKGROUND OF THE INVENTION

Venous access ports for the infusion and/or withdrawal of fluids from a patient are well-known. These devices are typically used for drug infusion or small amounts of blood aspiration. Where large flows of fluid are required, larger ports can be used such as for hemodialysis or plasmapheresis.

Some ports may be implanted subcutaneously. Implantable venous access ports have the advantage that they can remain within the patient for prolonged periods of time, permitting multiple use and decreasing the risk for associated infection. These ports typically provide a septum defining an access site for multiple needle sticks without the need to continuously search for new access sites, since the septum is comprised of material such as silicone elastomer that self-seals each time as a needle is withdrawn. These ports also each include a stem, or discharge port, that extends through a distal wall and that has a passageway therethrough; the stem is secured to the proximal end of a catheter so that the discharge port passageway is in fluid communication with the catheter lumen. One such catheter infusion port is disclosed in U.S. Pat. No. 6,113,572.

Other types of ports are in use, known as dual ports or multi-ports. These provide two or more internal septa and chambers, all corresponding to different lumens of the attached catheter via respective separate discharge ports or alternatively, separate passageways in a single stem for communication with separate lumens of a dual or multi-lumen catheter, such as in U.S. Pat. No. 5,360,407.

Such venous access ports are commonly circular in shape, or at least the chamber, or each chamber, is commonly circular, and the chamber floor is planar. As a result of the circular shape of a chamber and a planar chamber floor, the liquid injected during infusion exhibits a vortex behavior, and it has become noticeable that some liquid remains in the chamber by virtue of being near the center of the circular chamber's planar floor while the flow vortex occurs about the periphery of the chamber floor.

It is desirable to minimize the amount of liquid remaining in the chamber of a venous access port during infusion.

BRIEF SUMMARY OF THE INVENTION

The present invention is a venous access port having a chamber or fluid reservoir floor defined and shaped to be elevated in the center of the chamber, with sloping floor side surfaces extending to the chamber floor's periphery adjacent the chamber side wall. Preferably the chamber floor is convex or dome-shaped but the chamber floor may also be conical with a low-height apex and flat sloping side surfaces, and the chamber floor is preferably radiused adjacent the chamber side wall.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 2:
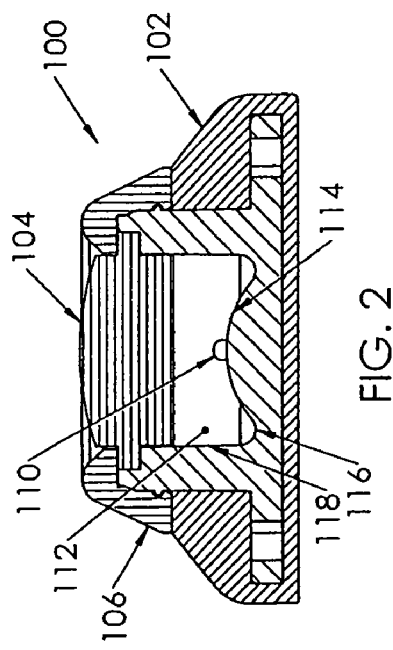
FIG. 2 is a cross-sectional view of the assembled port of FIG. 1 illustrating the present invention.

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Figure 1:
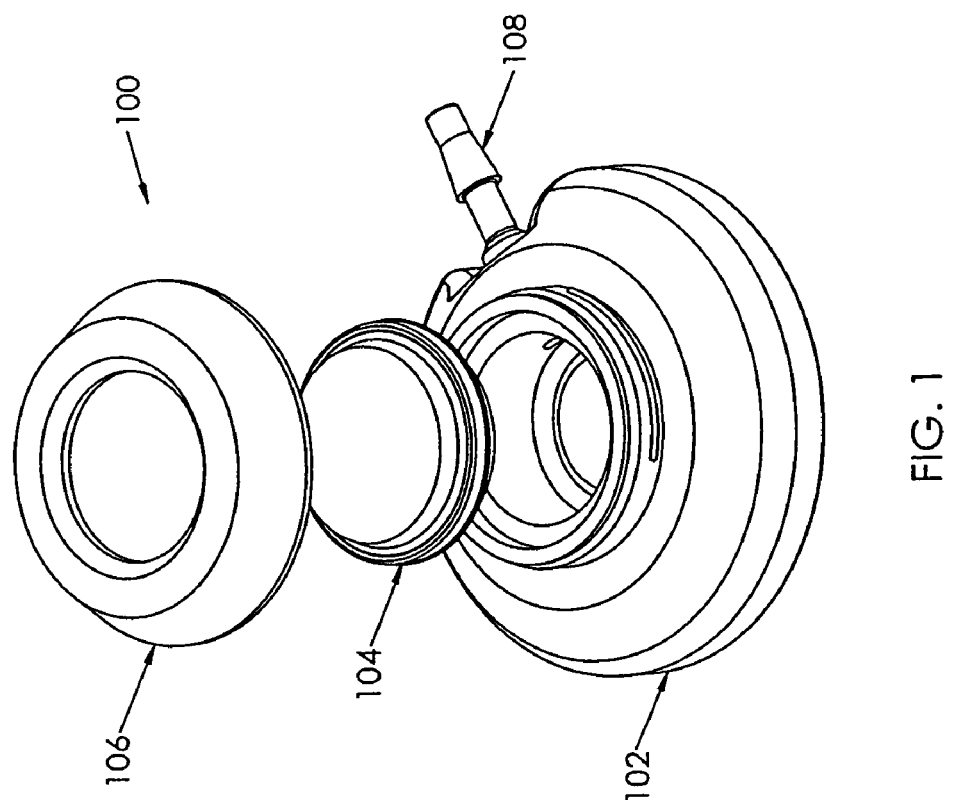
FIG. 1 is an exploded isometric view of a venous access port containing the present invention.

A first embodiment of venous access port 100 is illustrated in FIGS. 1 and 2 and includes a base 102, a septum 104 and a retention cap 106 that secures the septum to the base. A discharge port 108 extends from the base to which the proximal end of a catheter (not shown) is to be affixed, and a passageway 110 extends through discharge port 108 into the catheter lumen from the chamber 112 that is defined between the septum 104 and the base 102. Septum 104 is made of a self-sealing material such as preferably silicone elastomer, such that an infusion needle can be inserted through the septum for infusion of medication and upon withdrawal of the needle from the septum, the septum will immediately seal the hole through which the needle had extended.

In FIG. 2, chamber 112 is shown in cross-section. Chamber floor 114 is shown to be convex upwardly in the center of the chamber, and a vortex flow path 116 is seen to be defined about the periphery of the chamber. Passageway 110 is also seen that extends outwardly from the chamber and through the discharge port.

As a result of the convex shape of the chamber floor 114, infused medication will flow in its vortex flow path 116, and eventually as the level of fluid within the chamber diminishes, all liquid in the center of the chamber will perforce flow radially from the center toward the chamber side wall 118 and into the vortex path. With the elevated chamber floor of the present invention, clearance of the infused fluid is seen to begin sooner than with a flat floor design as no fluid can remain in the central region of the chamber floor.

Figure 3:
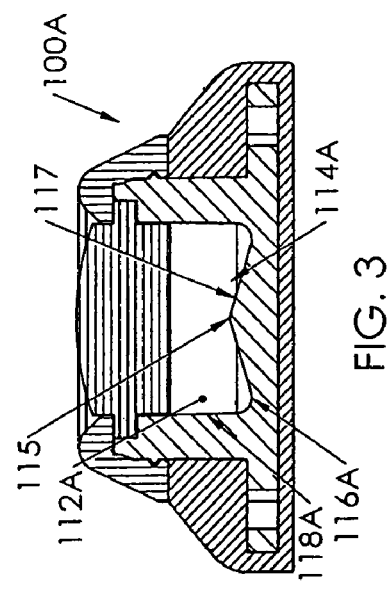
FIG. 3 is a cross-sectional view of an alternate embodiment of the present invention.

Alternatively, as seen in FIG. 3, the chamber floor 114A of a second embodiment of venous access port 100A may have a conical shape of low height, with an apical center point 115 and flat, sloping side surfaces 117 extending to the periphery of the chamber, again there defining a vortex flow path 116A, at which location the surfaces preferably are radiused to be tangent with the side wall 118A of the chamber.

It will be seen that it is preferred that the chamber floor of the present invention is elevated in its central region relative to the chamber floor periphery, and that the chamber floor has no level portions of substantial size. Variations of the present invention can easily be provided in chambers of dual chamber or multiple chamber venous access ports and achieve the benefits of the present invention of minimizing liquid remaining in the chamber after infusion.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A venous access port for implantation into a patient comprising:
   a port body comprising a discharge port, a vertical chamber side wall, and a chamber floor comprising a peripheral region and a central region elevated with respect to the peripheral region of the chamber floor, the vertical chamber side wall comprising a vertical portion that is straight in a vertical direction, the vertical portion perpendicular to the chamber floor; and
   a needle-penetrable septum affixed to the port body to seal a chamber formed by an entire space between the needle-penetrable septum, the vertical chamber side wall, and the chamber floor,
   wherein a portion of the needle-penetrable septum is disposed between portions of the vertical chamber side wall to fluidly seal the chamber.

2. The venous access port of claim 1 wherein the chamber floor is convex in the central region.

3. The venous access port of claim 1 wherein the chamber floor is conical upwardly to an apex and has relatively flat sloping side surfaces extending to the peripheral region of the chamber floor.

4. The venous access port of claim 3 wherein the peripheral region of the chamber floor is radiused to join the vertical chamber side wall.

5. The venous access port of claim 1 wherein the chamber floor has no level portion of substantial size.

6. The venous access port of claim 1, wherein the peripheral region of the chamber floor is radiused to join the vertical portion of the vertical chamber side wall.

7. The venous access port of claim 1, wherein an entirety of the vertical chamber side wall is straight in the vertical direction.

* * * * *